(12) United States Patent
Matsuura (10) Patent No.: US 11,369,334 B2
(45) Date of Patent: Jun. 28, 2022

(54) RADIOGRAPHIC IMAGING APPARATUS, RADIOGRAPHIC IMAGING SYSTEM, AND METHOD OF CONTROLLING RADIOGRAPHIC IMAGING APPARATUS

(71) Applicant: CANON KABUSHIKI KAISHA, Tokyo (JP)

(72) Inventor: Tomohiko Matsuura, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 170 days.

(21) Appl. No.: 16/718,780

(22) Filed: Dec. 18, 2019

(65) Prior Publication Data

US 2020/0205768 A1 Jul. 2, 2020

(30) Foreign Application Priority Data

Dec. 28, 2018 (JP) .............................. JP2018-247485

(51) Int. Cl.
*A61B 6/00* (2006.01)

(52) U.S. Cl.
CPC .............. *A61B 6/547* (2013.01); *A61B 6/463* (2013.01); *A61B 6/482* (2013.01); *A61B 6/548* (2013.01)

(58) Field of Classification Search
CPC ....... A61B 6/463; A61B 6/482; A61B 6/5205; A61B 6/542; A61B 6/547; A61B 6/548
See application file for complete search history.

(56) References Cited

FOREIGN PATENT DOCUMENTS

| JP | 2005-000369 A | 1/2005 |
| JP | 2017-192444 A | 10/2017 |
| JP | 2017192444 A | * 10/2017 |

OTHER PUBLICATIONS

English translation of JP2017/192444. (Year: 2017).*

* cited by examiner

*Primary Examiner* — Dani Fox
(74) *Attorney, Agent, or Firm* — Canon U.S.A., Inc. IP Division (57) ABSTRACT

A radiographic imaging apparatus configured to perform radiographic imaging using a plurality of sensors includes a region determination unit configured to analyze a reference image and determine a standard region in a region-of-interest of a subject in the reference image and a reference region in a region-of-non-interest of the subject in the reference image, and a determination unit configured to determine whether an amount of radiation with which the sensor of a region that corresponds to the standard region is irradiated reaches a standard value based on image data of the standard region, image data of the reference region, and a signal read from the sensor of a region that corresponds to the reference region.

13 Claims, 9 Drawing Sheets

RADIOGRAPHIC IMAGING APPARATUS, RADIOGRAPHIC IMAGING SYSTEM, AND METHOD OF CONTROLLING RADIOGRAPHIC IMAGING APPARATUS

BACKGROUND

Field of the Disclosure

The present disclosure relates to a radiographic imaging apparatus, a radiographic imaging system, and a method of controlling a radiographic imaging apparatus.

Description of the Related Art

In the field of medical radiographic imaging, a radiographic imaging apparatus is widely used that irradiates an examinee with radiation, acquires the radiation that transmits through the subject as a digital image signal using a radiation detection device, performs various types of image processing on the digital image signal, and then outputs the processed digital image signal as an image for diagnosis. In a case where the amount of radiation that is received by the radiation detection device is small, the percentage of noise components contained in the digital image signal increases. On the other hand, in a case where the amount of radiation that is received is excessively large, an artifact is generated due to saturation of each sensor of the radiation detection device. In both cases, the image quality of an image for diagnosis decreases, so that in order to acquire a suitable image for diagnosis, the amount of radiation that is received by the radiation detection device needs to be within an appropriate range. Thus, an apparatus that includes an automatic exposure control function (hereinafter, "AEC function") is used to control the amount of radiation that is received by the radiation detection device, and in a case where the amount of radiation that is received reaches a standard value, control is performed to end the radiation irradiation. To use the AEC function, a receptor field, which is a region for measuring the amount of radiation that is received, needs to be designated prior to radiation irradiation, and it is common to predetermine and store coordinates of the receptor field for each image capturing protocol (e.g., chest, front).

In recent years, an apparatus and method are known in which a radiation detection device has the above-described AEC function to simplify the configuration of a radiographic imaging apparatus, reduce cost, and increase convenience. Japanese Patent Application Laid-Open No. 2005-000369 discusses a method of performing AEC by designating coordinates (position) on a sensor array that correspond to a receptor field and monitoring a signal value of a sensor at the designated coordinates after radiation irradiation is started.

Further, Japanese Patent Application Laid-Open No. 2017-192444 discusses a specific method of monitoring a signal value of a sensor at designated coordinates after radiation irradiation is started. Specifically, a control line (so-called main scan line) of a monitoring target is periodically activated during radiation irradiation and the signal value of the sensor is acquired.

In the technique discussed in Japanese Patent Application Laid-Open No. 2017-192444, many signal components of the signal value of the sensor on the control line of the monitoring target are lost as a result of reading a monitoring signal, so that correction or complementing is needed at the time of acquiring a digital image signal. Since a receptor field of the AEC function is generally set in a region-of-interest of a subject, there arises an issue about a decrease in image quality of a region-of-interest as a result of correcting or complementing the digital image signal in the technique discussed in Japanese Patent Application Laid-Open No. 2017-192444.

SUMMARY

Some embodiments are directed to a technique for determining whether an amount of radiation with which a sensor of a region corresponding to a region-of-interest of a subject is irradiated reaches a standard value without causing a decrease in image quality of the region-of-interest.

According to an aspect of some embodiments, a radiographic imaging apparatus configured to perform radiographic imaging using a plurality of sensors includes a region determination unit configured to analyze a reference image and determine a standard region in a region-of-interest of a subject in the reference image and a reference region in a region-of-non-interest of the subject in the reference image, and a determination unit configured to determine whether an amount of radiation with which the sensor of a region that corresponds to the standard region is irradiated reaches a standard value based on image data of the standard region, image data of the reference region, and a signal read from the sensor of a region that corresponds to the reference region.

With various embodiments, it is determined whether an amount of radiation with which a sensor of a region corresponding to a region-of-interest of a subject is irradiated reaches a standard value without causing a decrease in image quality of the region-of-interest.

Further features of various embodiments will become apparent from the following description of exemplary embodiments with reference to the attached drawings.

DESCRIPTION OF THE EMBODIMENTS

Figure 1:
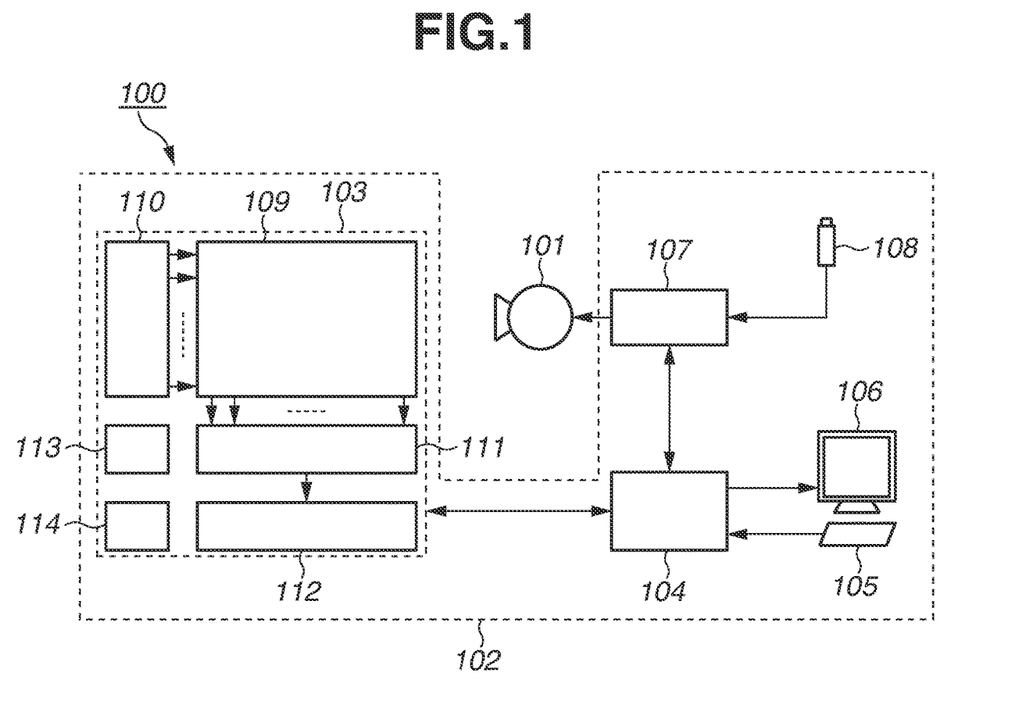
FIG. 1 illustrates an example of a configuration of a radiographic imaging system.

FIG. 1 illustrates an example of a configuration of a radiographic imaging system 100 according to a first exemplary embodiment. The radiographic imaging system 100 includes a radiation source 101 and a radiographic imaging apparatus 102. The radiographic imaging apparatus 102 includes an image capturing unit 103, a calculation unit 104, a terminal 105, a display unit 106, a radiation control unit 107, and an exposure switch 108.

Figure 2:
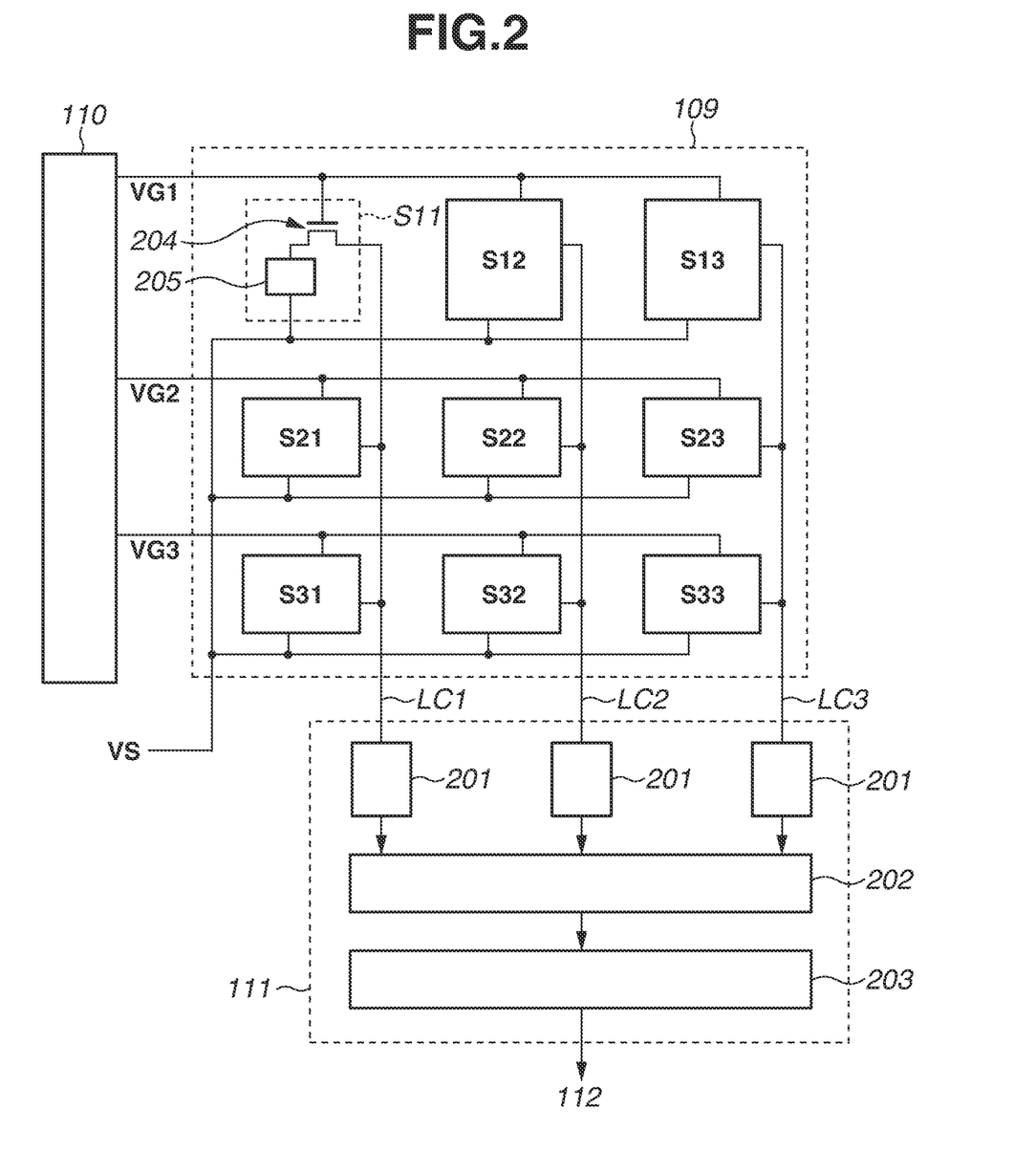
FIG. 2 illustrates an example of a configuration of a portion of an image capturing unit.

The image capturing unit 103 includes a sensor array 109, a driving unit 110, a reading unit 111, a processing unit 112, a control unit 113, and a voltage supply unit 114. The sensor array 109 includes a plurality of sensors S11 to S33 arranged in matrix as illustrated in FIG. 2 and generates an image signal based on radiation. Hereinafter, the sensors S11 to S33 will be referred to simply as "sensor S" when the sensors S11 to S33 are not specifically distinguished. The driving unit 110 drives the plurality of sensors S row by row. The reading unit 111 reads a signal (sensor signal) from the sensor S of each column that is driven by the driving unit 110. The processing unit 112 processes the read sensor signal. The control unit 113 controls synchronization of the units in the image capturing unit 103 using a reference signal, such as a clock signal. The voltage supply unit 114 supplies a power voltage to the units in the image capturing unit 103 so that each of the units operates properly.

The calculation unit 104 forms image data based on the sensor signal from the image capturing unit 103, performs incidentally necessary image processing, and outputs the resulting image data to the display unit (display) 106 so that the display unit 106 displays a radiographic image. Further, a user can input image capturing information to the calculation unit 104 via the terminal 105. The image capturing information is information about an examination target part of a subject (examinee such as a patient), personal information about the subject, a target amount of radiation, and other information necessary for radiographic imaging. The calculation unit 104 controls the image capturing unit 103 and the radiation control unit 107 based on the input image capturing information and manages image data acquired by radiographic imaging.

The calculation unit 104 can be a personal computer that stores a program or software configured to realize each operation of the radiographic imaging apparatus 102 or a calculation apparatus that includes an integrated circuit (e.g., application-specific integrated circuit (ASIC), field-programmable gate array (FPGA)).

The radiation control unit 107 drives the radiation source 101 in a case where, for example, the exposure switch 108 is pressed by the user while an irradiation start permission signal, which indicates that irradiation with radiation is possible, is input from the calculation unit 104. The radiation source 101 is a radiation generation apparatus and irradiates the sensor array 109 of the image capturing unit 103 of the radiographic imaging apparatus 102 with radiation. The radiation is, for example, X-rays and can be electromagnetic waves such as alpha-rays and beta-rays. The emitted radiation passes through a subject (not illustrated), enters the image capturing unit 103, and is detected by the sensors S of the sensor array 109. The radiographic imaging apparatus 102 performs radiographic imaging using the plurality of sensors S.

The configuration of the radiographic imaging system 100 is not limited to the above-described configuration and can be partially modified or eliminated or can additionally include another unit as needed for a purpose of use. Similarly, one function of one unit can be included in another unit, and/or some of the units can be integrated. For example, while the configuration in which the processing unit 112 and the calculation unit 104 are separately provided is described above as an example, the processing unit 112 and the calculation unit 104 can be realized as a single unit. Further, communication for inputting/outputting a signal between the image capturing unit 103 and the calculation unit 104 and between the calculation unit 104 and the radiation control unit 107 can be realized by wire, such as a local area network (LAN), or wirelessly, such as Wi-Fi communication.

FIG. 2 illustrates an example of a configuration of the sensor array 109, the driving unit 110, and the reading unit 111 of the image capturing unit 103 illustrated in FIG. 1.

The sensor array 109 includes the plurality of sensors S11 to S33 arranged as, for example, a matrix of three rows by three columns. The term "sensor Sij" refers to the sensor S at the ith row of the jth column, where i and j are integers of 1 to 3. For example, the term "sensor S11" refers to the sensor S at the first row of the first column, and the term "sensor S23" refers to the sensor S at the second row of the third column. While the configuration of three rows by three columns is described as an example for the purpose of simplifying the description, the number of rows and columns of an actual configuration is greater than the above-specified number (e.g., about 2800 rows by about 2800 columns in a case of a 17-inch sensor panel).

Each of the plurality of sensors S includes a detection element 205 and a transistor 204 and generates an image signal based on radiation. The detection element 205 detects radiation, and the transistor 204 connects the detection element 205 and a column signal line LC. In FIG. 2, the respective column signal lines LC that correspond to the first to third columns are specified as the column signal lines LC1 to LC3, to distinguish the column signal lines LC1 to LC3. Hereinafter, the column signal lines LC1 to LC3 will be referred to simply as "column signal line LC" when the column signal lines LC1 to LC3 are not specifically distinguished. In a case of a configuration in which the sensor S converts radiation into light and the light is photoelectrically converted (so-called indirect conversion type configuration), a scintillator is provided on the sensor array 109. In this case, a photoelectric conversion element, such as a p-intrinsic-n (PIN) sensor or metal-insulator-semiconductor (MIS) sensor, is used as the detection element 205, and a thin-film transistor is used as the transistor 204. In another example, the sensor S can be configured to convert radiation directly into an electric signal (so-called direct conversion type configuration).

The driving unit 110 drives the sensors S row by row by controlling the transistors 204 of the sensors S using a plurality of control lines VG1 to VG3 provided to the respective rows. Signals are read from the plurality of sensors S row by row. For example, the driving unit 110 supplies an activation signal to the sensors S of the first row via the control line VG1 and drives the sensors S of the first row. In this way, for example, sensor signals of the sensors S11, S12, and S13 are read by the reading unit 111 via the column signal lines LC1, LC2, and LC3, respectively.

The reading unit 111 includes a plurality of units 201, a multiplexer 202, and an output unit 203. The units 201 correspond to the respective columns. For example, each of the units 201 amplifies a sensor signal from the corresponding sensor S and then samples the amplified sensor signal. Details thereof will be described below. The multiplexer 202 sequentially transfers the sampled sensor signals column by column to the output unit 203. The output unit 203 includes, for example, a buffer circuit and an analog digital conversion device (ADC), and outputs each sensor signal as a digital signal to the processing unit 112.

Figure 3:
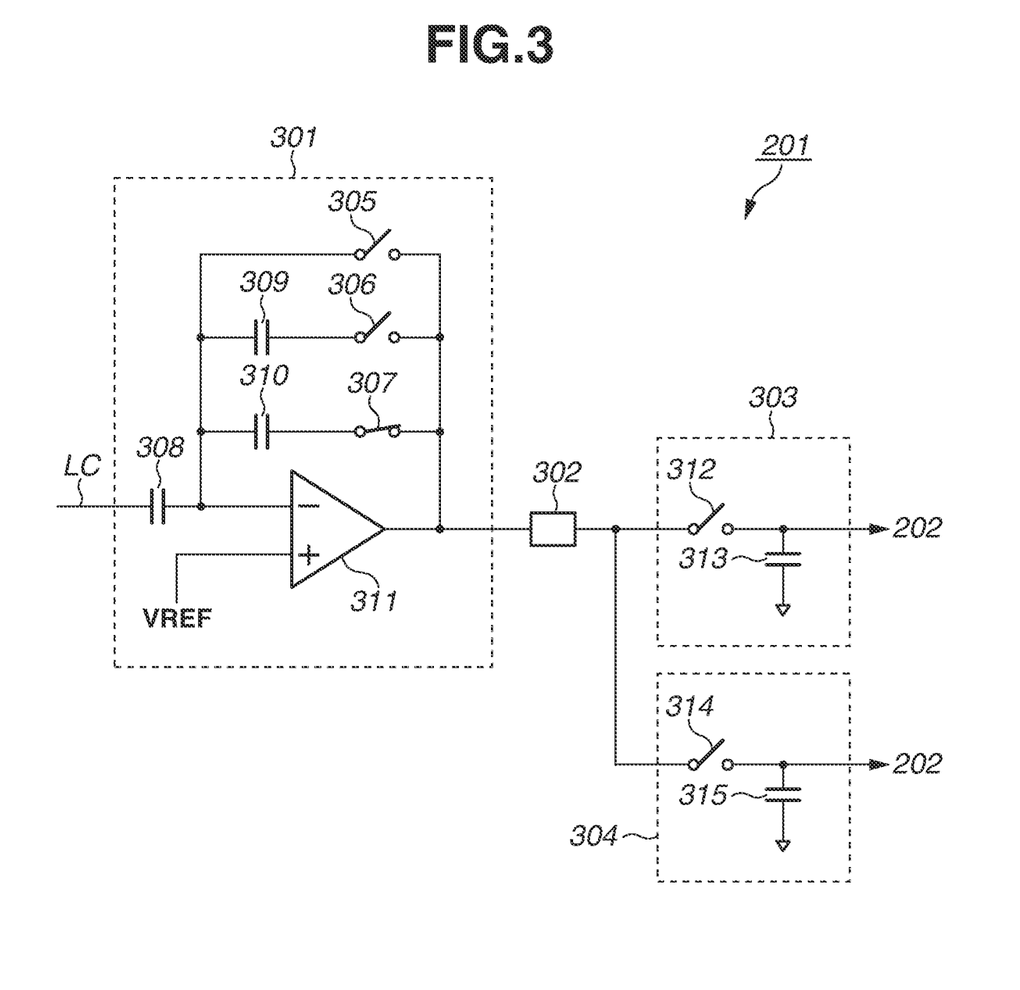
FIG. 3 illustrates an example of a configuration of a portion of a reading unit.

FIG. 3 illustrates an example of a configuration of the unit 201 in the reading unit 111 illustrated in FIG. 2. The unit 201 includes a signal amplification unit 301, a noise removal unit 302, a sampling unit 303, and a sampling unit 304. The signal amplification unit 301 includes switch elements 305 to 307, an input capacitor 308, feedback capacitors 309 and 310, and a differential amplification device 311. The input capacitor 308 is provided between an inversion input terminal (input terminal "−" in FIG. 3) of the differential amplification device 311 and the column signal line LC. A non-inversion input terminal (input terminal "+" in FIG. 3) of the differential amplification device 311 is connected to a node of a reference voltage VREF.

The switch element 305 is provided to a first feedback path between the inversion input terminal and an output terminal of the differential amplification device 311. The switch element 306 and the feedback capacitor 309 are connected in series and are provided to a second feedback path, which is a path parallel to the first feedback path. Further, the switch element 307 and the feedback capacitor 310 are connected in series and are provided to a third feedback path, which is a path parallel to the first and second feedback paths. A signal amplification factor of the signal amplification unit 301 can be changed by controlling the switch elements 306 and 307. If the switch element 305 is changed to an ON-state, the signal amplification unit 301 is reset (initialized). If the switch element 306 and/or the switch element 307 are/is changed to the ON-state while the switch element 305 is in an OFF-state, the signal amplification unit 301 amplifies the sensor signal of the column signal line LC at a signal amplification factor for the states of the switch elements 306 and 307.

The noise removal unit 302 is a low-pass filter that removes high-frequency noise components of the signal from the signal amplification unit 301. A resistor element is used as the noise removal unit 302.

The sampling units 303 and 304 are sampling circuits that perform correlated double sampling (CDS). Specifically, the sampling unit 303 includes a sampling switch 312 and a sampling capacitor 313 and samples an N signal from the signal amplification unit 301 reset by the switch element 305. The sampling unit 304 includes a sampling switch 314 and a sampling capacitor 315 and samples an S signal amplified by the signal amplification unit 301 in a reset-cancelled state of the switch element 303. The multiplexer 202 transfers the N signal and the S signal to the output unit 203, and the output unit 203 performs analog/digital conversion (AD conversion) using the difference between the N signal and the S signal as a signal component.

Figure 4:
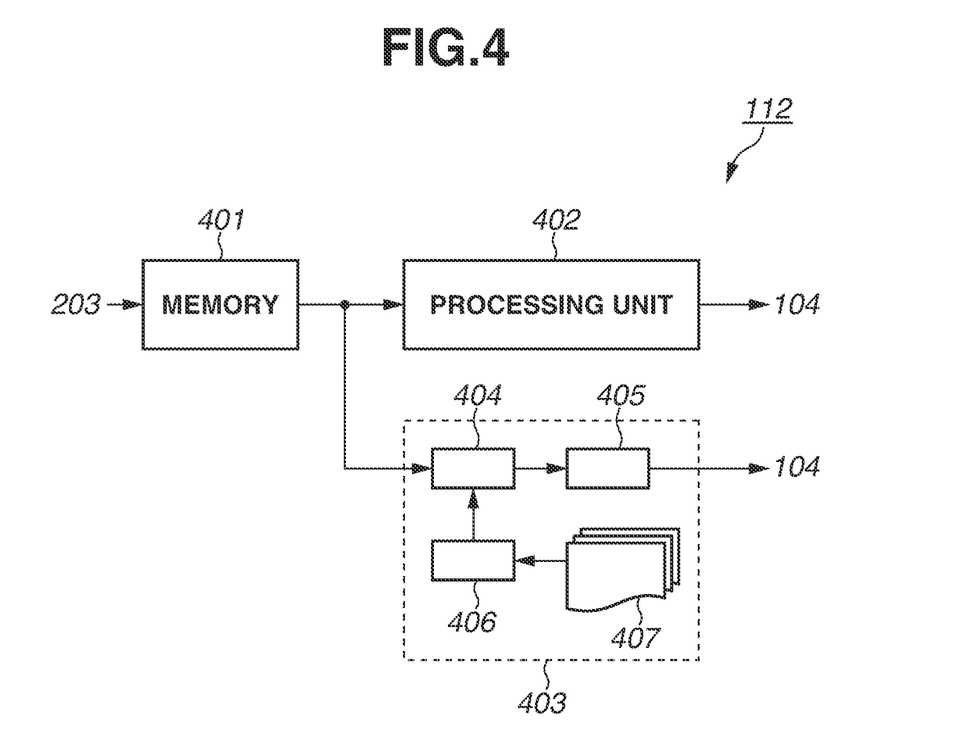
FIG. 4 illustrates an example of a configuration of a processing unit.

FIG. 4 illustrates an example of a configuration of the processing unit 112 illustrated in FIG. 1. The processing unit 112 includes a memory 401 and processing units 402 and 403. The radiographic imaging system 100 includes a reading operation mode and an accumulation operation/automatic exposure control (AEC) mode as operation modes. Details thereof will be described below. In the operation modes, the processing unit 112 stores a digital signal input from the output unit 203 in the memory 401.

In the reading operation mode, sensor signals (digital signals) for forming a radiographic image are read from the sensors S11 to S33 by the reading unit 111, and the read sensor signals are stored in the memory 401. Then, the processing unit 402 reads the sensor signals from the memory 401, performs signal processing (e.g., correction processing) on the read sensor signals, and outputs the processed sensor signals to the calculation unit 104.

In the accumulation operation/AEC mode, the radiographic imaging system 100 ends the irradiation with radiation in a case where the amount of applied radiation reaches a standard value after the irradiation with radiation is started and before the sensor signals are read from the sensors S in the reading operation mode. In this way, the radiographic imaging system 100 can control the amount of applied radiation within a suitable range. In the accumulation operation/AEC mode, sensor signals (digital signals) are read from some of the sensors S11 to S33 as signals for monitoring for performing AEC and are temporarily stored in the memory 401. In the other sensors S, electric charges corresponding to the applied radiation are accumulated. Hereinafter, the signals for monitoring that are read to perform AEC will be referred to simply as "monitor signals" to simplify the description. The processing unit 403 reads the monitor signals from the memory 401 and performs processing for performing AEC on the read monitor signals. In this point of view, the processing unit 403 or the processing unit 112 including the processing unit 403 can be expressed as an image capturing control unit for performing AEC in radiographic imaging.

The processing unit 403 includes a correction unit 404, a determination unit 405, a setting unit 406, and a reference image data group 407. The setting unit 406 sets a parameter necessary for performing AEC with respect to image data of one frame selected from the reference image data group 407 based on information input via the terminal 105 by a user. Details thereof will be described below.

While the configuration in which reference image data is selected from the reference image data group 407 is described as an example in the present exemplary embodiment, a method for the selection is not limited to the above-described example. For example, reference image data may be selected (or extracted) as appropriate by the setting unit 406 based on data attribute information (identification (ID)) or may be selected (or input) directly by a user operation of the terminal 105.

The correction unit 404 corrects the monitor signals stored in the memory 401 using the parameter set by the setting unit 406. The determination unit 405 determines whether the signal values of the corrected monitor signals reach the standard value, and outputs a signal for ending the irradiation with radiation based on the determination result. This process will be described in detail below with reference to FIGS. 5 and 6.

Figure 5:
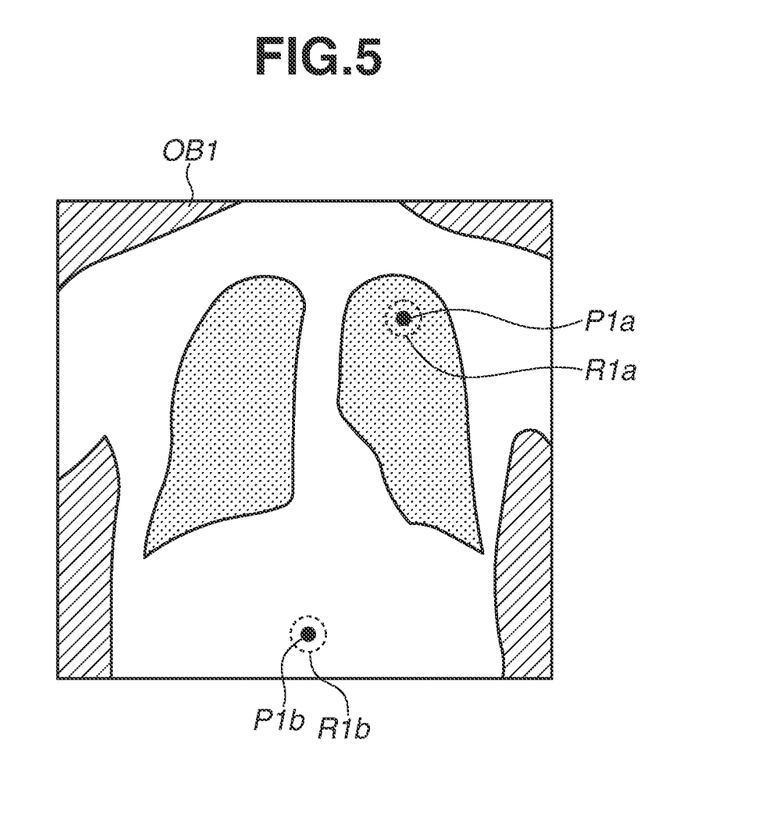
FIG. 5 illustrates an example of an automatic exposure control (AEC) setting.

FIG. 5 illustrates a radiographic image (hereinafter, "reference image") based on the image data selected from the reference image data group 407 illustrated in FIG. 4. The reference image is displayed on, for example, the display unit 106 such that the user can input information necessary for radiographic imaging using the terminal 105 while referring to the reference image. The reference image is, for example, an image of a subject (front image of chest of human body) OB1.

The user selects (designates) a standard point P1a for stabilizing an image quality or an amount of received radiation in a region-of-interest of the subject OB1 in the reference image. For example, the standard point P1a specifies a right upper or left upper lung field, or another part can be selected depending on an image capturing target part or purpose of image capturing.

After selecting the standard point P1a, the user selects a reference point P1b at a position that is in a region-of-non-interest of the subject OB1 and on a control line (so-called main scan line) on which the region-of-interest does not exist. The direction of the control line is uniquely determined depending on the design of the image capturing unit 103. For example, in a case where the control line of the image capturing unit 103 is in a horizontal direction, the user selects a portion of an abdominal region at a height (row) that does not include the lung field, which is the region-of-interest of the subject OB1, as the reference point P1b. The reference point P1*b* is not limited to that described above and may be another portion that is in the region-of-non-interest and on a control line on which the region-of-interest does not exist.

Figure 6:
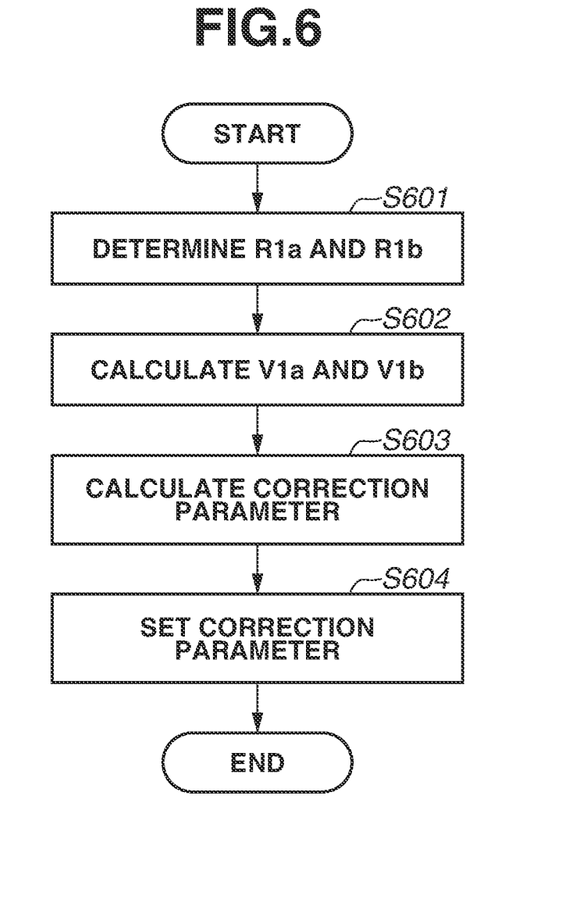
FIG. 6 is a flowchart illustrating an example of an operation of a setting unit.

FIG. 6 is a flowchart illustrating a control method of the setting unit 406 and illustrates a process of setting a correction parameter from the standard point P1*a* and the reference point P1*b* selected by the user using a reference image.

First, in S601, the setting unit 406 determines a standard region R1*a* and a reference region R1*b* (refer to FIG. 5) as local respective regions that envelop the standard point P1*a* and the reference point P1*b*. The standard region R1*a* is a region in the region-of-interest of the subject OB1 in the reference image in FIG. 5. The reference region R1*b* is a region in the region-of-non-interest of the subject OB1 in the reference image in FIG. 5. For example, the setting unit 406 determines a circular region having a radius of 15 mm with the standard point P1*a* being the center of the circular region and a circular region having a radius of 15 mm with the reference point P1*b* being the center of the circular region as the standard region R1*a* and the reference region R1*b*, respectively. The standard region R1*a* and the reference region R1*b* are not limited to those described above and may have any other shape and/or size.

Next, in S602, the setting unit 406 calculates a standard representative value V1*a*, which is a representative value of image data of the standard region R1*a*, and a reference representative value V1*b*, which is a representative value of image data of the reference region R1*b*. For example, the setting unit 406 uses a mean value of image data values in the standard region R1*a* as the standard representative value V1*a* and uses a mean value of image data values in the reference region R1*b* as the reference representative value V1*b*. The standard representative value V1*a* and the reference representative value V1*b* are not limited to those described above, and any other calculation methods or statistical values (e.g., median value) may be used.

Next, in S603, the setting unit 406 calculates the ratio between the standard representative value V1*a* and the reference representative value V1*b* as the correction parameter. Next, in S604, the setting unit 406 sets the correction parameter to the correction unit 404.

The user refers to the reference image illustrated in FIG. 5 and selects the standard point P1*a* and the reference point P1*b* and then performs radiographic imaging of a subject OB2. The subject OB2 can be the same person as the subject OB1 or a different person from the subject OB1. Details thereof will be described below.

There is a possible situation where a standard region R2*a*, which is a standard region of the subject OB2 and corresponds to the standard region R1*a* of the subject OB1, is set as a receptor field and a monitor signal is read from the sensor S in the receptor field and AEC is performed when radiographic imaging of the subject OB2 is performed. However, since the standard region R2*a* is in the region-of-interest of the subject OB2, if the image capturing unit 103 having the AEC function is used, the signal value of the control line that has the sensor S in the receptor field is decreased or lost, causing a decrease in image quality of a portion of the region-of-interest, as described above.

Thus, the image capturing unit 103 sets a reference region R2*b*, which is a reference region of the subject OB2 and corresponds to the reference region R1*b* of the subject OB1, as a receptor field, reads a monitor signal from the sensor S in the receptor field, and performs AEC. The reference region R2*b* is outside the region-of-interest of the subject OB2, likewise the reference region R1*b* of the subject OB1, so that a decrease in image quality is allowed to some extent.

The plurality of sensors S is irradiated with radiation through the subject OB2. The image capturing unit 103 reads a monitor signal from the sensor S of the reference region R2*b* corresponding to the reference region R1*b* among the plurality of sensors S. The correction unit 404 corrects the monitor signal read from the sensor S corresponding to the reference region R2*b* based on the correction parameter set by the setting unit 406. As described above, the correction parameter is a parameter that is set based on the reference image, which is an image of the subject OB1, and is the ratio between the standard representative value V1*a* and the reference representative value V1*b*. The correction unit 404 corrects the monitor signal using the correction parameter to thereby estimate the signal value of the sensor S corresponding to the standard region R2*a* and estimate the amount of radiation with which the standard region R2*a* is irradiated (the amount of radiation that passes through the standard region R2*a*). The standard region R2*a* is a region of the plurality of sensors S that corresponds to the standard region R1*a*. The sensor S of the standard region R2*a* and the sensor S of the reference region R2*b* are sensors of different rows from each other. An estimation value of the monitor signal from the sensor S that corresponds to the standard region R2*a* corresponds to an estimated amount of radiation with which the standard region R2*a* is irradiated, and is calculated based on the monitor signal from the sensor S that corresponds to the reference region R2*b*, the standard representative value V1*a*, and the reference representative value V1*b*.

The determination unit 405 determines whether to end the irradiation with radiation based on the signal value of the monitor signal corrected by the correction unit 404 (i.e., the estimation value of the signal from the sensor S that corresponds to the standard region R2*a*). Specifically, the determination unit 405 cumulatively adds the signal values of the monitor signals corrected using a correction unit 404 and calculates a cumulative total value of the estimation values of the signals from the sensor S that corresponds to the standard region R2*a*. The cumulative addition can be performed by the correction unit 404 or another calculation unit in place of the determination unit 405. The determination unit 405 determines whether the radiation with which the sensor S that corresponds to the standard region R2*a* is irradiated reaches the standard value by determining whether the cumulative total value of the estimation values of the signals from the sensor S that corresponds to the standard region R2*a* reaches the standard value. In a case where the determination unit 405 determines that the cumulative total value reaches the standard value, the determination unit 405 outputs a signal for ending the radiation irradiation. The determination unit 405 determines whether the amount of radiation with which the sensor S of the region that corresponds to the region-of-interest is irradiated reaches the standard value based on image data of the region-of-interest of the subject, image data of the region-of-non-interest of the subject, and the signals read from the sensor S of the region that corresponds to the region-of-non-interest. In this way, AEC is realized.

While the example is described in which the monitor signals from the sensor S that corresponds to the reference region R2*b* are corrected by the image capturing unit 103 using the correction parameter and AEC is performed based on whether the cumulative total value of the signal values of the corrected monitor signals reaches the standard value, AEC is not limited to the above-described example. For example, the image capturing unit 103 can set a target value different from the standard value based on the correction parameter and realize AEC based on whether the cumulative total value of the monitor signals from the sensor S that corresponds to the reference region R2b reaches the target value. Specifically, the image capturing unit 103 corrects the target value using the correction parameter and in this case, the correction unit 404 does not correct the monitor signals from the sensor S that corresponds to the reference region R2b. The determination unit 405 determines whether the amount of radiation with which the sensor S of the standard region R2a is irradiated reaches the standard value by determining whether the cumulative total value of the signals read from the sensor S of the reference region R2b reaches the target value. The target value is a value that is based on the correction parameter (the ratio between the representative value of the image data of the standard region R1a and the representative value of the image data of the reference region R1b).

The image capturing unit 103 can realize AEC based on whether the cumulative total value reaches the target value. At this time, the image capturing unit 103 can predict a timing to end the radiation irradiation based on an intermediate calculation result and perform AEC based on a result of the prediction. Specifically, the calculation processing for realizing AEC does not necessarily have to be performed after waiting until the cumulative total value reaches the target value.

While the subjects OB2 and OB1 are desirably the same person in order to increase the accuracy of the correction by the correction unit 404, in a case where the subject OB2 is, for example, a new patient, a reference image of another subject having great relevance or high similarity to the subject OB2 can be used. In an example, the subject OB1 of the reference image is a subject having a height within a range from 10% smaller to 10% larger than the height of the subject OB2. In another example, the subject OB1 of the reference image is a subject having a weight within a range from 10% less to 10% more than the weight of the subject OB2. In yet another example, the subject OB1 of the reference image is a subject of an age within a range from 10% less to 10% more than the age of the subject OB2. Further, in yet another example, the subject OB1 of the reference image is a subject of the same sex as the subject OB2. While the height, weight, age, and sex are described as examples of a relevance/similarity determination standard, a body-fat percentage or body-mass index (BMI) can be referenced, or the determination can be performed based on a combination of two or more of the conditions.

The above-described processing for AEC is performed by the processing unit 403 in the processing unit 112, but as described above, part of the function of the processing unit 112 can be realized by the calculation unit 104, and the processing for AEC can also be realized by the calculation unit 104. Specifically, the above-described processing for AEC can be realized by an external apparatus connected to the image capturing unit 103. The external apparatus is specifically a processing apparatus that includes a processor configured to perform signal processing or information processing, and can be referred to as a signal processing apparatus or information processing apparatus.

Figure 7:
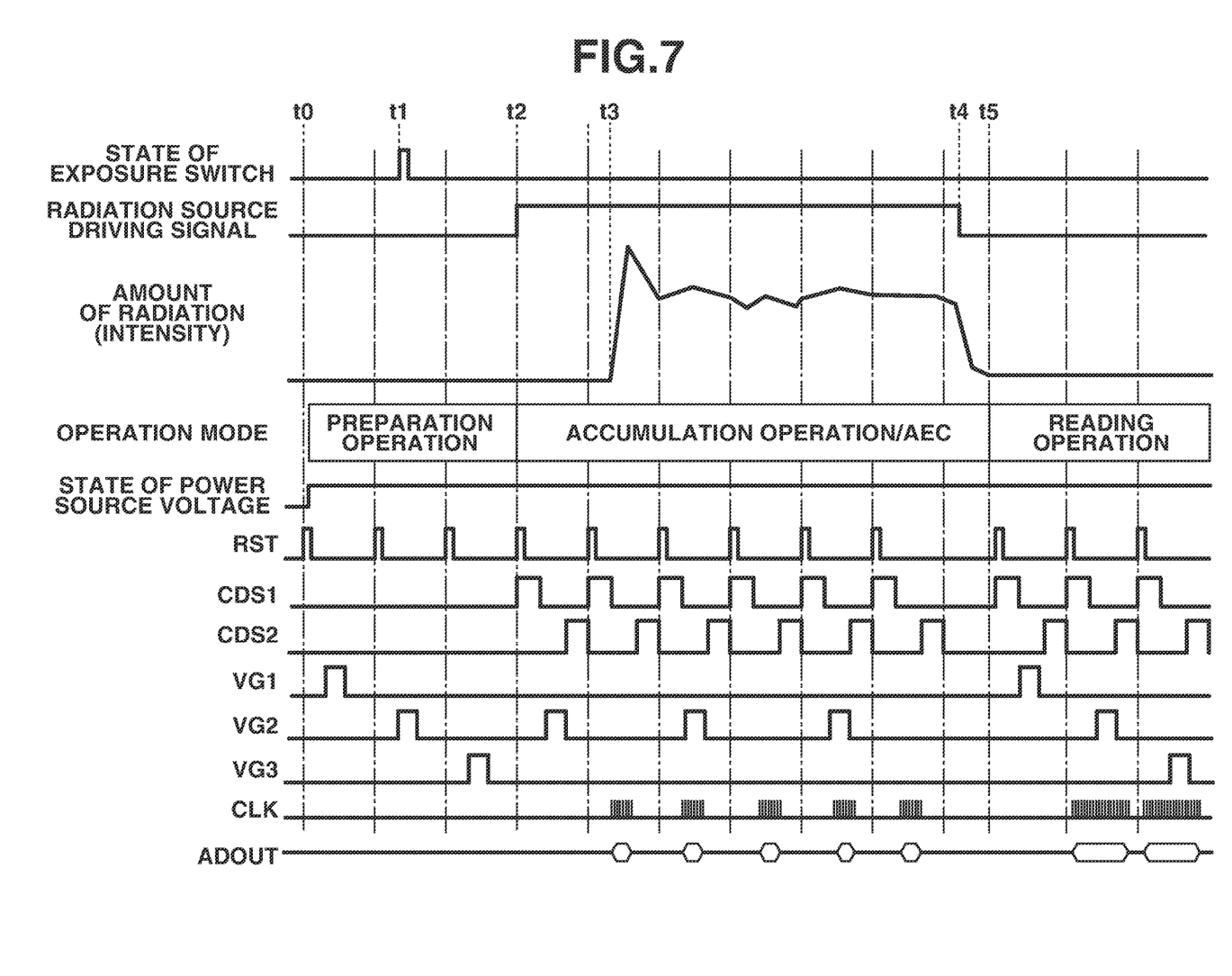
FIG. 7 is a timing chart illustrating an example of an operation of a radiographic imaging system.

FIG. 7 is a timing chart illustrating an example of a control method of the radiographic imaging system 100. In FIG. 7, a horizontal axis is a time axis, and a state of the exposure switch 108, a radiation source driving signal for driving the radiation source 101, an amount (intensity) of radiation from the radiation source 101, an operation mode, a state of a power source voltage, and signals are illustrated.

In the state of the exposure switch 108, a low level (L-level) indicates that the exposure switch 108 is not pressed, whereas a high level (H-level) indicates that the exposure switch 108 is pressed. If the radiation source driving signal is changed to the H-level, the radiation source 101 is driven. The amount of radiation indicates the intensity (amount of irradiation per unit time) of radiation that is generated by the radiation source 101 when the radiation source driving signal is changed to the H-level. The operation mode is an operation mode of the radiographic imaging system 100 and includes a preparation operation mode from the supply of the power source voltage to the radiographic imaging system 100 to a change to a state in which radiographic imaging can be started besides the reading operation mode and the accumulation operation/AEC mode.

A signal RST is a control signal of the switch element 305 in FIG. 3, and if the signal RST is changed to the H-level, the switch element 305 is changed to the ON-state, and the signal amplification unit 301 is reset. A signal CDS1 is a control signal of the switch element 312 in FIG. 3, and if the signal CDS1 is changed to the H-level, the switch element 312 is changed to the ON-state, and sampling is performed by the sampling unit 303. A signal CDS2 is a control signal of the switch element 314 in FIG. 3, and if the signal CDS2 is changed to the H-level, the switch element 314 is changed to the ON-state, and sampling is performed by the sampling unit 304. Signals VG1 to VG3 correspond to the signals of the control lines VG1 to VG3 in FIG. 2 and are given the same reference numerals as the control lines VG1 to VG3 for simplicity. For example, if the signal VG2 is changed to the H-level, the sensors S of the second row are driven. A signal CLK is a clock signal for use in AD conversion by the ADC of the output unit 203. A signal ADCOUT indicates a digital signal acquired by the above-described AD conversion.

During the preparation operation mode from time t0 to time t2, the image capturing unit 103 sequentially activates the signals VG1 to VG3 while supplying the signal RST of a H-level pulse at predetermined intervals and sequentially resets the sensors S of the first to third rows. While the example in which the sensors S of the first to third rows are reset once is described, actually, resetting is performed a plurality of times (e.g., about 10 seconds). In a case where all the sensors S are sufficiently reset, a notification that radiation irradiation can be started is provided to the user, and the user presses the exposure switch 108. The timing of the press of the exposure switch 108 by the user is referred to as "time t1".

At time t2, as the resetting of the sensors S of the third row is finished, the radiation control unit 107 shifts the operation mode to the accumulation operation/AEC mode and changes the radiation source driving signal to the H-level. In response thereto, the image capturing unit 103 alternately activates the signals CDS1 and CDS2, activates the signal VG2 therebetween, and reads the monitor signals from the sensors S21 to S23 of the second row. The sensors S21 to S23 of the second row are the sensor S of the row that includes the sensor S corresponding to the reference region R2b. The monitor signals are AD-converted by the output unit 203 in FIG. 2, and the converted signals are stored in the memory 401 in FIG. 4, and thereafter, the processing unit 403 performs processing for AEC. During the accumulation operation/AEC mode from time t2 to time t5, the sensors S11 to S13 and S31 to S33 of the first and third rows accumulate charges corresponding to radiation.

At time t3, as the radiation source driving signal is changed to the H-level at time t2, the radiation source 101 increases the amount of radiation. Thus, the signal value of the monitor signal read from time t2 to time t3 is substantially zero.

At time t4, the processing unit 403 determines that the amount of radiation irradiation reaches the standard value, and outputs a signal for ending the radiation irradiation. Then, the radiation control unit 107 changes the radiation source driving signal to the L-level. Specifically, the correction unit 404 corrects the monitor signals from the sensors S21 to S23, which correspond to the reference region R2b, using the correction parameter. If the determination unit 405 determines that the cumulative total value of the signal values of the corrected monitor signals reaches the standard value, the radiation control unit 107 changes the radiation source driving signal to the L-level. Specifically, if the determination unit 405 determines that a value obtained by the processing unit 403 by cumulatively adding the estimation values of the signal values of the sensor S that corresponds to the standard region R2a of the subject OB2 reaches the standard value, the radiation control unit 107 changes the radiation source driving signal to the L-level. As the radiation source driving signal is changed to the L-level, the radiation source 101 ends the radiation irradiation.

At time t5, the image capturing unit 103 shifts the operation mode to the reading operation mode and sequentially reads a sensor signal (image signal) from every sensor S. Specifically, the image capturing unit 103 alternately activates the signals CDS1 and CDS2 while supplying the signal RST of the H-level pulse at predetermined intervals, sequentially activates the signals VG1 to VG3 therebetween, and sequentially reads the sensor signals from the sensors S of the first to third rows. As described above, the read sensor signals are stored in the memory 401, subjected to predetermined signal processing by the processing unit 402, and then output to the calculation unit 104. At this time, many of the signal components of the sensor signals from the sensors S of the second row are lost as a result of the reading of the monitor signals for AEC at time t2 to time t4. Thus, the processing unit 402 or the calculation unit 104 corrects or complements the sensor signal read from the sensor S of the second row of the reference region R2b based on the sensor signals of the adjacent sensors S.

As described above, the setting unit 406 refers to the reference image, selects the standard point P1a in the region-of-interest of the subject OB1, and acquires the standard representative value V1a. Further, the setting unit 406 selects the reference point P1b at a position that is in the region-of-non-interest of the subject OB1 and on a control line on which the region-of-interest does not exist, and acquires the reference representative value V1b. In radiographic imaging of the subject OB2, the processing unit 403 performs AEC based on the correction parameter, which is the ratio between the standard representative value V1a and the reference representative value V1b, and the monitor signal from the sensor S that corresponds to the reference region R2b. Specifically, the processing unit 403 determines whether the standard region R2a is irradiated with an appropriate amount of radiation.

With the image capturing unit 103 with the AEC function, a decrease in image quality of the receptor field occurs. Thus, the image capturing unit 103 designates the reference region, which is a portion of the region-of-non-interest of the subject, as the receptor field without designating the standard region, which is a portion of the region-of-interest of the subject. Then, the image capturing unit 103 estimates the monitor signal from the sensor S that corresponds to the standard region by correcting the monitor signal from the sensor S that corresponds to the reference region, and performs AEC. In this way, the image capturing unit 103 can perform AEC as appropriate so that the standard region is irradiated with an amount of radiation within a target range without causing a decrease in image quality of the standard region, which is a portion of the region-of-interest.

Figure 8:
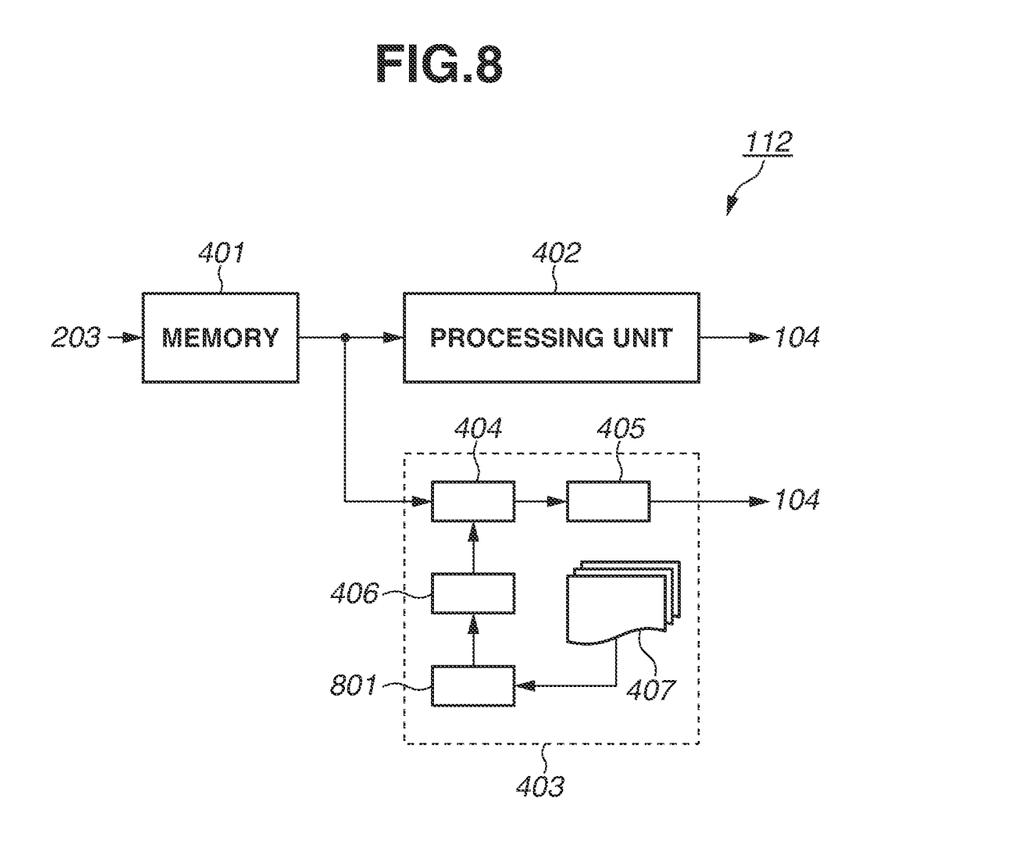
FIG. 8 illustrates an example of a configuration of a processing unit.

FIG. 8 illustrates an example of a configuration of the processing unit 112 in FIG. 1 according to a second exemplary embodiment. A point at which the present exemplary embodiment is different from the first exemplary embodiment will be described below. The processing unit 112 in FIG. 8 includes a region determination unit 801 in addition to the processing unit 112 in FIG. 4. The region determination unit 801 is provided in the processing unit 403. The region determination unit 801 automatically determines the standard region R1a and the reference region R1b in FIG. 5 without a user operation based on image data of one frame selected from the reference image data group 407 and information about an image capturing target part.

Figure 9:
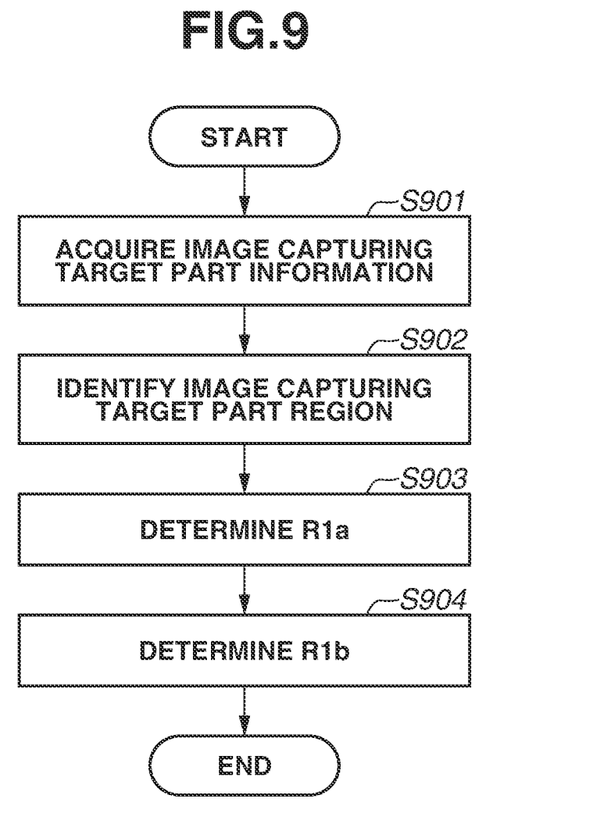
FIG. 9 is a flowchart illustrating an example of an operation of a region determination unit.

FIG. 9 is a flowchart illustrating a control method of the region determination unit 801. First, in S901, the region determination unit 801 acquires information about the image capturing target part from an external apparatus (generally referred to as hospital information system (HIS) or radiology information system (RIS)) that manages an image capturing order.

Next, in S902, the region determination unit 801 analyzes image data (reference image) of one frame selected from the reference image data group 407 based on the acquired information about the image capturing target part and identifies a region of the image capturing target part. For example, the image data is analyzed by a method that uses a knowledge-based algorithm based on the shape, position, and size of an anatomical structure of a human body. An image data analysis method is not limited to that described above and, for example, a method that analyzes a histogram of an image or a method that uses machine learning can be used.

Next, in S903, the region determination unit 801 determines a circular region having a radius of 15 mm with the center of gravity of the identified image capturing target part region being the center of the circular region, as the standard region R1a. The shape and size of the standard region R1a are not particularly limited as in the first exemplary embodiment.

Next, in S904, the region determination unit 801 determines a circular region having a radius of 15 mm with the center of the circular region at a position that is outside the image capturing target part region identified in S902 and on a control line on which the image capturing target part region does not exist, as the reference region R1b. In a case where there are a large number of candidates for the reference region R1b in the reference image, the region determination unit 801 determines a region that is geometrically farthest from the standard region R1a, as the reference region R1b. The shape and size of the reference region R1b and a method of determining the reference region R1b are not particularly limited.

Next, the setting unit 406 sets a correction parameter for AEC based on the standard region R1a and the reference region R1b as in S602 to S604 in FIG. 6. S602 to S604 are similar to those in the first exemplary embodiment.

The example in which the correction parameter for AEC is set without a user operation is described above. For example, the processing unit 403 can present the standard region R a and the reference region R1b determined by the region determination unit 801 as an initial setting to the user, change or not change the initial setting depending on the user determination, and set the correction parameter for AEC using the changed or unchanged initial setting.

Further, the processing unit 403 can store the standard region R1a and the reference region R1b that are previously determined or the correction parameter for AEC that is previously set, for a reference image. In this case, when the reference image is selected as a new reference image, the processing unit 403 can use the stored previous standard region R a and the stored previous reference region R1b or the stored previous correction parameter for AEC, or the processing unit 403 can present the stored previous standard region R1a and the stored previous reference region R1b or the stored previous correction parameter for AEC to the user as an initial setting.

In the first and second exemplary embodiments, the configurations are described in which each of the plurality of sensors S has a function as a sensor for image capturing (e.g., function as a pixel) and a function as a sensor for AEC that reads the above-described monitor signals. Alternatively, the image capturing unit 103 can be configured such that most of the plurality of sensors S have a fixed function as a sensor for image capturing and some of the rest of the sensors S have a fixed function as a sensor for AEC.

Other Exemplary Embodiment

Also, some embodiments are realizable by a process in which a program configured to realize one or more functions of the above-described exemplary embodiments is supplied to a system or apparatus via a network or storage medium and one or more processors of a computer of the system or apparatus read and execute the program. Further, some embodiments are realizable by a circuit (e.g., ASIC) configured to realize one or more functions.

While various exemplary embodiments are described above as examples, the scope of some embodiments is not limited to the examples, and changes to part thereof can be made within the spirit of the disclosure. Further, each term in the present specification is used merely for the purpose of describing the exemplary embodiments, and it is apparent that the scope of some embodiments are not limited to the exact meaning of the term and can encompass the equivalents thereof.

Other Embodiments

Some embodiment(s) can also be realized by a computer of a system or apparatus that reads out and executes computer-executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer-executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer-executable instructions. The computer-executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present disclosure has described exemplary embodiments, it is to be understood that some embodiments are not limited to the disclosed exemplary embodiments. The scope of the following claims is to be accorded the broadest interpretation so as to encompass all such modifications and equivalent structures and functions.

This application claims priority to Japanese Patent Application No. 2018-247485, which was filed on Dec. 28, 2018 and which is hereby incorporated by reference herein in its entirety.

What is claimed is:

1. A radiographic imaging apparatus configured to perform radiographic imaging using a plurality of sensors connected to a plurality of control lines, the radiographic imaging apparatus comprising:
   a region determination unit configured to analyze a reference image and determine a standard region in a region-of-interest of a subject in the reference image and a reference region in a region-of-non-interest of the subject in the reference image; and
   a determination unit configured to determine whether an amount of radiation with which the sensor of a region that corresponds to the standard region is irradiated reaches a standard value based on image data of the standard region, image data of the reference region, and a signal read from the sensor of a region that corresponds to the reference region,
   wherein the sensor of the region that corresponds to the standard region and the sensor of the region that corresponds to the reference region are connected to different control lines.

2. The radiographic imaging apparatus according to claim 1, further comprising a first correction unit configured to estimate a signal of the sensor of the region that corresponds to the standard region by correcting the signal read from the sensor of the region that corresponds to the reference region based on the image data of the standard region and the image data of the reference region,
   wherein the determination unit determines whether a cumulative total value of the estimated signal of the sensor of the region that corresponds to the standard region reaches the standard value.

3. The radiographic imaging apparatus according to claim 2, wherein the first correction unit corrects the signal read from the sensor of the region that corresponds to the reference region based on a ratio between a representative value of the image data of the standard region and a representative value of the image data of the reference region.

4. The radiographic imaging apparatus according to claim 1, wherein the determination unit determines whether the amount of radiation with which the sensor of the region that corresponds to the standard region is irradiated reaches the standard value by determining whether a cumulative total value of the signal read from the sensor of the region that corresponds to the reference region reaches a target value that is based on the image data of the standard region and the image data of the reference region.

5. The radiographic imaging apparatus according to claim 1, wherein the determination unit determines whether the amount of radiation with which the sensor of the region that corresponds to the standard region is irradiated reaches the standard value by determining whether a cumulative total value of the signal read from the sensor of the region that corresponds to the reference region reaches a target value that is based on a ratio between a representative value of the image data of the standard region and a representative value of the image data of the reference region.

6. The radiographic imaging apparatus according to claim 1,
wherein the plurality of sensors is arranged in matrix, and a signal is read from the plurality of sensors row by row, and
wherein the sensor of the region that corresponds to the standard region and the sensor of the region that corresponds to the reference region are sensors of different rows from each other.

7. The radiographic imaging apparatus according to claim 1, wherein the plurality of sensors is irradiated with radiation through a subject that is the same as the subject of the reference image.

8. The radiographic imaging apparatus according to claim 1,
wherein the reference image is an image of a first subject, wherein the plurality of sensors is irradiated with radiation through a second subject, and
wherein the first subject satisfies at least one of:
a condition that a height of the first subject is within a range from 10% smaller to 10% larger than a height of the second subject,
a condition that a weight of the first subject is within a range from 10% less to 10% more than a weight of the second subject,
a condition that an age of the first subject is within a range from 10% less to 10% more than an age of the second subject, and
a condition that a sex of the first subject is same as a sex of the second subject.

9. The radiographic imaging apparatus according to claim 1, wherein in a case where the determination unit determines that the amount of radiation with which the sensor of the region that corresponds to the standard region is irradiated reaches the standard value, the determination unit outputs a signal for ending the radiation irradiation.

10. The radiographic imaging apparatus according to claim 9, wherein an image signal is read from the plurality of sensors after the determination unit outputs the signal for ending the radiation irradiation.

11. The radiographic imaging apparatus according to claim 10, further comprising a second correction unit configured to correct the signal that is read from the sensor of the region that corresponds to the reference region among the image signal read from the plurality of sensors.

12. A radiographic imaging system comprising:
the radiographic imaging apparatus according to claim 1; and
a radiation generation apparatus configured to irradiate the radiographic imaging apparatus with radiation.

13. A method of controlling a radiographic imaging apparatus configured to perform radiographic imaging using a plurality of sensors connected to a plurality of control lines, the method comprising:
analyzing a reference image and determining a standard region in a region-of-interest of a subject in the reference image and a reference region in a region-of-non-interest of the subject in the reference image; and
determining whether an amount of radiation with which the sensor of a region that corresponds to the standard region is irradiated reaches a standard value based on image data of the standard region, image data of the reference region, and a signal read from the sensor of a region that corresponds to the reference region,
wherein the sensor of the region that corresponds to the standard region and the sensor of the region that corresponds to the reference region are connected to different control lines.

* * * * *